United States Patent [19]

Izumi

[11] 4,366,818

[45] Jan. 4, 1983

[54] VACUUM TYPE URINATING AID

[75] Inventor: Yoshitaka Izumi, Tokyo, Japan

[73] Assignee: Kimura Bed Mfg. Company Limited, Tokyo, Japan

[21] Appl. No.: 179,885

[22] Filed: Aug. 20, 1980

[30] Foreign Application Priority Data

| Oct. 12, 1979 [JP] | Japan | 54-140958[U] |
|---|---|---|
| Oct. 12, 1979 [JP] | Japan | 54-140959[U] |
| Oct. 12, 1979 [JP] | Japan | 54-140961[U] |
| Oct. 12, 1979 [JP] | Japan | 54-140962[U] |
| Oct. 12, 1979 [JP] | Japan | 54-140963[U] |

[51] Int. Cl.$^3$ .............................................. A61F 5/44
[52] U.S. Cl. .................................. 128/295; 128/276; 4/305
[58] Field of Search ........................ 200/61.04, 61.05; 324/71 CP; 73/861.08, 861.12; 340/852; 128/295, 276, 277, 278, 138 A, 138 R, 691, 692; 4/302, 304, 305, 313, DIG. 3, 406

[56] References Cited

U.S. PATENT DOCUMENTS

| 3,406,569 | 10/1968 | Rohmann | 73/861.12 |
| 3,751,736 | 8/1973 | Egli | 4/DIG. 3 |
| 4,180,091 | 12/1979 | Hanley | 137/238 |
| 4,281,655 | 8/1981 | Terauchi | 128/278 |

FOREIGN PATENT DOCUMENTS

| 992462 | 10/1951 | France | 128/295 |
| 903156 | 8/1962 | United Kingdom | 324/71 CP |
| 223258 | 10/1968 | U.S.S.R. | 128/295 |

*Primary Examiner*—Richard J. Apley
*Assistant Examiner*—J. L. Kruter
*Attorney, Agent, or Firm*—Wenderoth, Lind & Ponack

[57] ABSTRACT

A suction type urinating aid comprises a urine transport tube connected at one end through a urine detecting cylinder with a urine receiver provided with an air suction hole and a urine suction opening to be applied to a urinating region, and connected, at the other end, with a urine tank. A suction tube communicating to a vacuum device is connected to the upper part of the urine tank. The urine detecting cylinder is composed of a pair of electrodes placed at an interval inside an electrically insulating cylinder. Wires connected to the respective electrodes are connected to a control device of the vacuum device, so that when urine exists in the urine detecting cylinder, electric current flowing through the urine between the electrodes may be detected by the control device, to start the vacuum device by the control device.

2 Claims, 6 Drawing Figures

VACUUM TYPE URINATING AID

BACKGROUND OF THE INVENTION

The present invention relates to a suction type urinating aid.

There are people who must be assisted in urinating in bed. These people include the old lying in bed, serious patients, patients suffering from incontinence of urine, who cannot control their urination as soon as they feel a desire to urinate, and patients who cannot go to the toilet alone.

To attain the objective of assistance, there is known an apparatus in which a receiver applied to the urinating region of the patient to receive his urine is connected with a tank to collect the urine through a tube. However, with the conventional apparatus, the urine received by the receiver is dropped into the tank through said tube simply by gravity, and therefore the tube and the tank must be placed below the receiver, to permit urine to be dropped. For example, if the patient changes his position, causing the tube to be placed even partially above the receiver, the urine in the tube flows back into the receiver, to soak the patient and bedclothes inconveniently. Such a conventional apparatus is disadvantagely rstricted in the place of use and urinating pose.

SUMMARY OF THE INVENTION

The urinating aid of the present invention receives the urine of the patient in a urine receiver applied to his urinating region, and transports it to a urine tank through a urine transport tube forcedly together with air by vacuum, thereby overcoming the disadvantage of the conventional apparatus. In other words, even when the urine transport tube and the urine tank cannot be placed below the urine receiver, the present invention allows urine to be transported into the urine, tank, without causing it to flow back.

Thus, the present invention permits a patient to urinate, while lying in bed by reasonable application of a vacuum device. Particularly in the present invention, to vacuum device is started automatically by detecting urination, for very simple operation and reliable use.

BRIEF DESCRIPTION OF THE DRAWINGS

The present invention is described below in detail with reference to the accompanying drawings which show preferred embodiments.

DETAILED DESCRIPTION OF THE INVENTION

Figure 1:
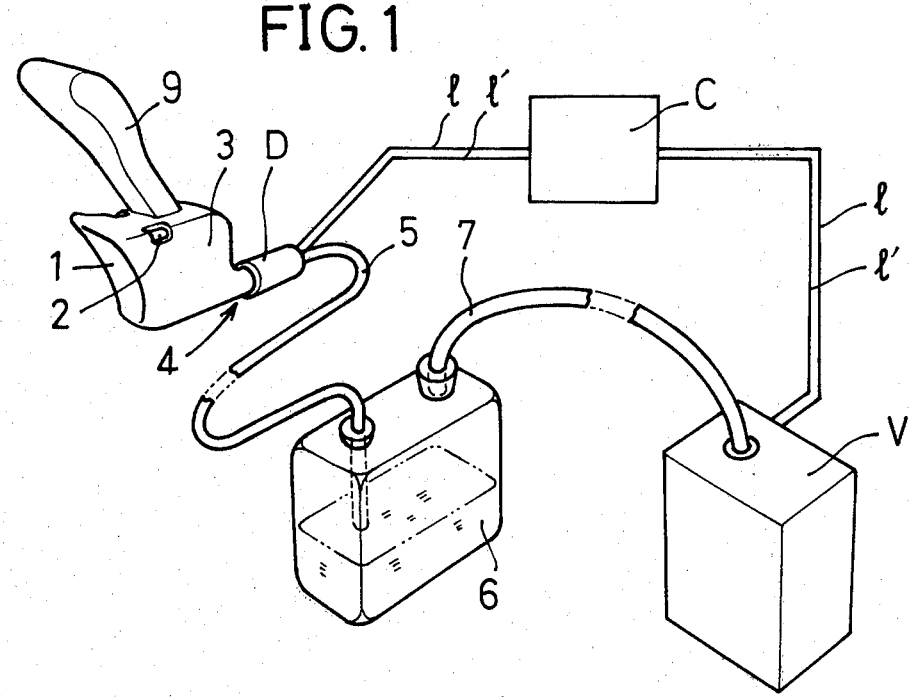
FIG. 1 is an illustrative perspective view showing one embodiment of the general composition of the suction type urinating aid of the present invention.

FIG. 1 shows an embodiment of the general composition of the vacuum type urinating aid of the present invention. Such suction type urinating aid has a urine receiver 3 provided with a urine suction opening 1 at the front side and an air suction hole 2 at a suitable location. A urine transport tube is connected, at one end, to a urine outlet 4 of the urine receiver 3 through a urine detecting cylinder D, and is connected, at the other end, with a urine tank 6 which is further connected, at its upper part, with a suction tube 7 communicating to a vacuum device V. In the drawing, urine tank 6 is separated from vacuum device V, but they can be of course arranged solidly in a proper housing.

Urine detecting cylinder D has a pair of electrodes e and e' arranged at an interval inside an electrically insulating cylinder 8, and wires 1 and 1' respectively connected to electrodes e and e' are connected to a control device C of vacuum device V. Control device C detects the electric current flowing between electrodes e and e' through urine when the urine exists in urine detecting cylinder D, and starts vacuum device V. The detailed composition will be described later.

This embodiment of the present invention is operated as described below.

Figure 2:
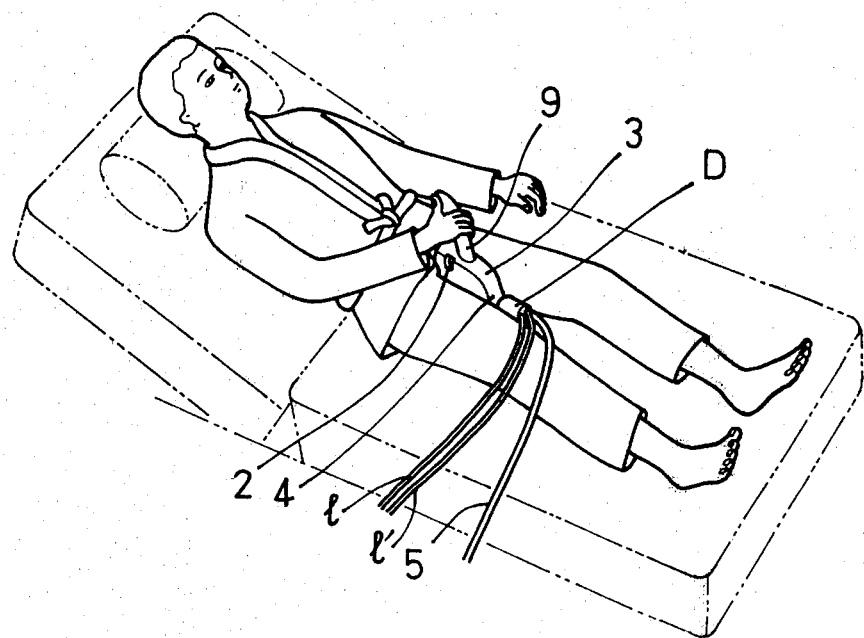
FIG. 2 is an illustrative perspective view of a main portion showing the manner of applying the suction type urinating aid of the present invention.

When a patient feels a desire to urinate, he can grasp a handle 9 provided at a proper position of the urine receiver 3, as shown in FIG. 2, to apply the urine suction opening 1 to his urinating region, for simply urinating into said urine receiver 3.

The urine discharged in this way flows from the urine outlet 4 into the urine detecting cylinder D, wetting the area between the pair of electrodes e and e', and decreases the resistance value between the electrodes e and e'. Thus, the electric current flowing through the urine between electrodes e and e' is detected through the wires 1 and 1' by the control device C, to start the suction device V. If the suction device V is started in this way, vacuum pressure is applied to the urine transport tube 5 through the suction tube 7 and the urine tank 6. Therefore, the urine received by the urine receiver 3 is sucked forcedly from the urine outlet 4 through the urine detecting cylinder D into the urine transport tube 5, together with and by air sucked into urine receiver 3 from air suction hole 2 and the clearance between urine suction opening 1 and the urinating region of the patient. The urine is then fed into the urine tank 6. In this case, since the suction tube 7 communicating with the suction device V is connected to the upper part of the urine tank 6, urine is not sucked by the suction tube 7, but is collected in the urine tank 6 and is separated from air. Furthermore, since the urine receiver 3 has the air suction hole 2 formed separately from the urine suction opening 1, hole 2 prevents the urine suction opening 1 from adhering to the urinating region of the patient, which would otherwise be caused by the vacuum pressure, to improve the feeling of using the aid, and even if the urine suction opening 1 is in close contact with the urinating region without any clearance, the volume of air required to carry urine can be always secured by the air sucked through air suction hole 2. The opening of the air suction hole 2 may be made freely adjustable. Thus, the present invention has a feature that even when the urine transport tube 5 and the urine tank 6 are not placed below the urine receiver 3, urine does not flow back, thereby allowing urination always without any trouble, since the urine received by the urine receiver 3 is forcedly sucked together with the sucked air through the urine outlet 4 into the urine transport tube 5 and is discharged into the urine tank 6.

As a particular feature of the present invention, since the vacuum device V is automatically started by detecting the existence of urine by the urine detecting cylinder D, the operation is simple, and the patient himself can use the aid easily, being free from the inconvenience of forgetting to turn on a switch or failing to turn the switch on in the time as in case of using a manual switch. Moreover, since the urine detecting cylinder D is provided near the urine outlet 4 of the urine receiver 3, it cannot happen that the urine discharged into the urine receiver 3 is spilled before the vacuum device V is started.

Figure 6:
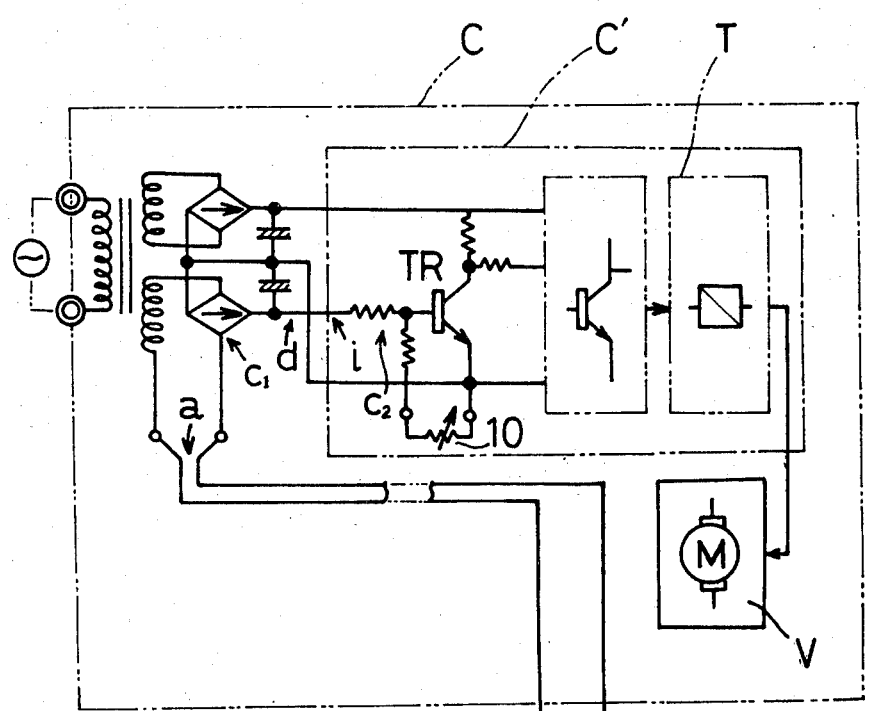
FIG. 6 is an illustration showing a schematic embodiment of a control device of the present invention.
Figure 6:
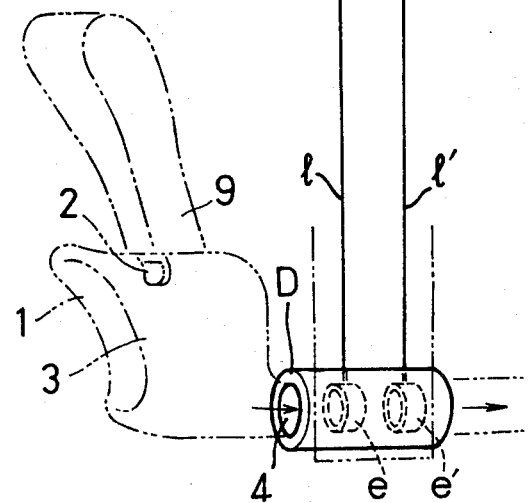

Electrodes e and e' can have any shape as long as they enable electric current to flow through the urine as mentioned before, but the ring shape illustrated has an effect that even a small amount of urine can be reliably detected, since urine flowing in any portion of the urine detecting cylinder D can wet the area between electrodes e and e'. As for the control device C which starts the vacuum device V by detecting the electric current flowing through urine between electrodes e and e', such device C can be any suitable arrangement. An embodiment of the control device C shown in FIG. 6 is described below. The control device C is provided with a rectifier circuit $C_1$. The wires l and l' from said pair of electrodes e and e' are connected in series to said alternating current side a of rectifier circuit $C_1$, and the direct current side d of rectifier circuit $C_1$ is connected to the input i of a proper switching circuit C'.

If urine flows through the urine outlet 4 into the urine detecting cylinder D, to wet the area between the pair of electrodes e and e', in accordance with the operation mentioned before, the resistance value between electrodes e and e' decreases. Therefore between electrodes e and e's, viz. on the AC side a of a rectifier circuit $C_1$, AC detection current flows through the urine, and at the same time, on the DC side d of the rectifier circuit $C_1$, a DC urine detection signal is generated, to be applied to the switching circuit C' as a control signal. An example of switching circuit C' is a transistor switching circuit as iillustrated, and the urine detection signal is applied to a transistor base circuit $C_2$ of such transistor switching circuit. Switching circuit C' can be constructed in any way as long as it allows switching by a DC urine detection signal. Symbol 10 indicates a variable resistor for adjusting the urine detecting sensitivity.

In this embodiment, the existence of urine passing through the urine detecting cylinder D is electrically detected, as mentioned above, to generate a DC urine detection signal, for operating the switching circuit C', thereby controlling the vacuum device V. In this case, since the urine detection current flowing between the electrodes e and e' through the urine is alternating current, electrodes e and e'are not corroded electrolytically, thereby assuring a long electrode life.

Figure 3:
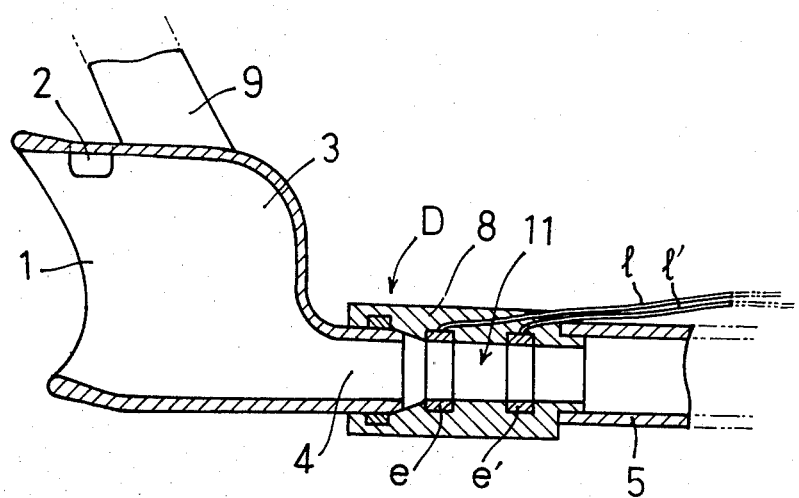
FIGS. 3 to 5 are illustrative longitudinal sectional views showing three embodiments of a main portion of the present invention.
Figure 4:
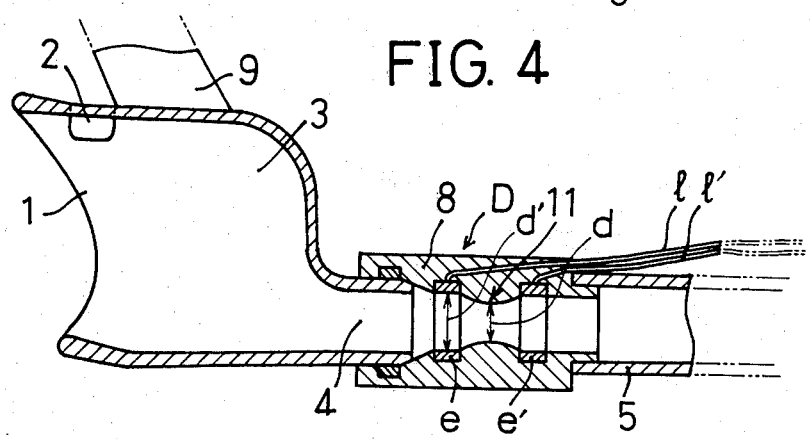
Figure 5:
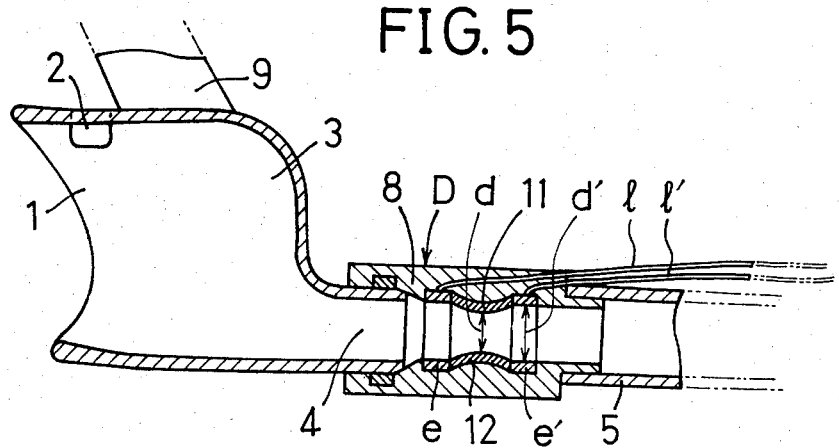

After the end of urination, when all the urine in the urine receiver 3 is sucked through the urine outlet 4 and the urine detecting cylinder D into the urine transport tube 5, to leave no urine between the pair of electrodes e and e', the resistance value between electrodes e and e' increases again. This increase of resistance value between the electrodes e and e' turns off the switching circuit C', to stop the operation of the vacuum device V. The urine which wetted the area between the electrodes e and e', to decrease the resistance is removed from said urine detecting cylinder D with the termination of urination and moves into the urine transport tube 5. However, if the inner diameter d of the cylinderical portion 11 between the electrodes e and e' is larger than or the same as the inner diameter d' of the electrodes e (FIG. 3) and e', urine may remain as a thin film by surface tension between the electrodes e and e' since the resistance between the electrodes e also and e' is kept low, the vacuum device V may continue operation inconveniently even after the termination of urination. In the embodiments shown in FIGS. 4 and 5, since the inner diameter of the cylindrical portion 11 between the electrodes e and e' is made smaller than the inner diameter d' of the electrodes e and e', urine does not remain between the electrodes e thus and e', enabling the vacuum device V to be stopped automatically and reliably after the end of urination. Moreover, as shown in the embodiment of FIG. 5, this effect can be made more remarkable, by applying a surface coating with a material low in critical surface tension and low wettability, for example polytetrafluoroethylene, etc., or making the cylinder itself by such a material. In the meantime, immediately after urine is no longer detected after the end of urination, urine exists in the transport urine tube 5 arranged after the urine detecting cylinder D. Since the motor of the vacuum device V keeps rotating for a while by inertia even if it is turned off electrically, suction is continued for a while through the volume of sucked urine decreases. Therefore, when urine no longer exists between the electrodes e and e', urine existing in the rear part of the urine transport tube 5 can be discharged into the urine tank 6. To ensure this state thoroughly, an off delay timer T may be provided in said switching circuit C', in order that the operation of vacuum device V may be automatically maintained for a duration set by the off delay timer, even after the resistance between electrodes e and e' increases to secure an OFF state, or another urine detecting cylinder (not illustrated) may be provided at a location adjacent to the urine tank 6, in addition to the urine detecting cylinder D adjacent to urine receiver 3, in order that the vacuum device V may be operated by the logical sum of urine detecting cylinder D and the another urine detecting cylinder, to prevent the back flow of urine in the transport tube 5.

As described above in detail, the suction type urinating aid of the present invention has a feature that even when the urine transport tube and the urine tank cannot be placed below the urine receiver, urine can be collected perfectly in the urine tank without causing the urine to flow back, and therefore that a patient can urinate, lying in bed, etc., with no restriction on the place of use or urinating pose, since the urine received by the urine receiver applied to the urinating region of the patient is transported forcedly together with air in the urine transport tube by suction to the urine tank. Furthermore, as an effect of the present invention, since the vacuum device is automatically started bydetecting the existence of urine by the urine detecting cylinder, the operation is simple, and the patient himself can use the aid easily, being free from erroneous operation such as forgetting to turn on a switch as in the case of using a manual switch. As a further feature, since the urine detecting cylinder is provided near the urine outlet of the urine receiver, it cannot happen that the urine discharged into the urine receiver is spilled before the vacuum device is started.

Thus, the present invention enables such people to urinate, using the aid in bed when necessary, as the old lying in bed, serious patients suffering from the incontinence of urine, who cannot control their urination as soon as they feel a desire to urinate, and patients who cannot go to the toilet alone, irrespective of whether they live in private houses or hospitals. The quality of nursing for such patients thus can be improved remarkably.

What is claimed is:

1. A suction type urinating aid comprising:

a urine receiver having a urine suction opening adapted to be applied to the urinating region of a subject to receive therefrom urine, an air suction hole, and a urine outlet;

an electrically insulating cylinder connected to said urine outlet;

a urine tank;

a urine transport tube connected between said cylinder and said urine tank;

vacuum device means connected to said urine tank for drawing air into said urine receiver through said air suction hole therein and for drawing said air and any urine in said urine receiver through said urine outlet, said cylinder and said urine transport tube into said urine tank;

control means connected to said vacuum device means for controlling the operation therof;

detector means located in said cylinder, electrically connected to said control means, for detecting the presence of any urine in said cylinder and for causing said control means to operate said vacuum device means for drawing said air and urine from said urine receiver, said detector means comprising first and second ring-shaped electrodes positioned iinteriorly of said cylinder, said first and second electrodes being spaced from each other axially of said cylinder and electrically insulated from each other by said cylinder, said electrodes being positioned such that when urine exists in said cylinder, an electric current will flow through such urine between said electrodes and will be detected by said control means to start operation of said vacuum device means; and the inner diameter of a cylindrical portion of said cylinder between said electrodes being equal to the inner diameter of said electrodes.

2. A vacuum suction type urinating aid as claimed in claim 1, wherein said control means includes a rectifier circuit, and wires extending from said electrodes are connected in series to the alternating current side of said rectifier circuit, so that alternating current may flow through urine between said electrodes, to generate a DC urine detection signal at the direct current side of said rectifier circuit.

* * * * *